United States Patent
Weinstock

(10) Patent No.: US 11,864,834 B1
(45) Date of Patent: Jan. 9, 2024

(54) MULTI-TILED PLENOPTIC SYSTEM FOR THE DETECTION AND CORRECTION OF OCULAR DEFECTS AND FOR IMPROVED FOVEATED RENDERING

(71) Applicant: Soliddd Corp., New York, NY (US)

(72) Inventor: Neal Weinstock, New York, NY (US)

(73) Assignee: SOLIDDD CORP., New York, NY (US)

( * ) Notice: Subject to any disclaimer, the term of this patent is extended or adjusted under 35 U.S.C. 154(b) by 0 days.

(21) Appl. No.: 18/101,452

(22) Filed: Jan. 25, 2023

(51) Int. Cl.
*A61B 3/14* (2006.01)
*A61B 3/00* (2006.01)

(52) U.S. Cl.
CPC .............. *A61B 3/14* (2013.01); *A61B 3/0025* (2013.01); *A61B 3/0041* (2013.01)

(58) Field of Classification Search
None
See application file for complete search history.

(56) References Cited

U.S. PATENT DOCUMENTS

| | | | | |
|---|---|---|---|---|
| 2015/0257639 A1* | 9/2015 | Manquez Hatta | ....... | A61B 3/14 351/246 |
| 2015/0313467 A1* | 11/2015 | Sakai | ..................... | A61B 3/152 351/208 |
| 2017/0007115 A1* | 1/2017 | Samec | ................. | A61B 3/1015 |
| 2023/0012806 A1* | 1/2023 | Shin | ..................... | A61B 5/7275 |

* cited by examiner

*Primary Examiner* — Nicholas J Lee
(74) *Attorney, Agent, or Firm* — Ference & Associates LLC

(57) ABSTRACT

One embodiment provides a method, including: obtaining, utilizing at least one image capture device, at least one image of an eye of a user; identifying, from the at least one image, a plurality of characteristics of the eye, wherein at least one of the characteristics includes a position of a pupil of the eye; generating, based upon the plurality of characteristics of the eye, a plurality of images, wherein each of the plurality of images is generated for a portion of the eye; and presenting, utilizing at least one display device, the plurality of images to the eye, wherein each of the plurality of images is presented to a portion of the eye corresponding to the image generated for the given portion of the eye. Other embodiments are described herein.

20 Claims, 7 Drawing Sheets

MULTI-TILED PLENOPTIC SYSTEM FOR THE DETECTION AND CORRECTION OF OCULAR DEFECTS AND FOR IMPROVED FOVEATED RENDERING

FIELD OF THE INVENTION

The present disclosure generally relates to a visual aid device, more particularly, to a visual aid device that can identify a condition of a user's eyes and provide a display that allows for improved viewing of a field of view.

BACKGROUND OF THE INVENTION

Many people have eye conditions that result in a reduced viewing ability, for example, near sightedness, far sightedness, eye diseases (e.g., glaucoma, macular degeneration, etc.), and/or the like. Furthermore, many people have health problems which might be detected by a physician's examination of the eye, but that go undetected because of lack of access to a physician's care. Devices commonly worn in front of the eye, for example, virtual-reality headsets, may feature sensors that look into the eye for purposes such as gaze tracking. Gaze tracking may be combined with visual aid devices, for example, glasses, contacts, sunglasses, digital devices that allow for the manipulation of information displayed on a display (e.g., changing contrast, changing brightness, changing the size of the information, etc.), and/or the like, and can assist a person in more accurately viewing a visual field. In other words, visual aid devices can be used to account for the viewing deficiencies caused by the eye conditions, thereby allowing the user to see better or more closely to a person who does not suffer from such eye conditions. Generally, this may be referred to as correcting the eye condition. However, it should be noted that the eye condition itself is not cured or healed, but rather the way the person sees is corrected. As soon as the person is no longer utilizing the visual aid device, the visual ability of the person returns to the capacity resulting from the eye condition(s) of the user.

SUMMARY OF THE INVENTION

Visual aid devices may be particularly helpful for correcting a visual field for some eye conditions, for example, far sightedness, near sightedness, a combination of both, light sensitivities, and/or the like. While conventional visual aid devices can be utilized to assist in correcting a viewing field for some eye conditions, visual aid devices are not available for correcting a viewing field for all eye conditions. For example, visual aid devices to address eye diseases including macular degeneration, glaucoma, severe astigmatism, retinitis pigmentosa, central serious retinopathy, and/or the like, generally either do not exist, or at best, for these conditions, may utilize a display that allows the person to adjust video to add contrast, change color, add what is commonly known as "picture-in-picture" to show a redundant section of the overall image in an additional area, add brightness, provide text-to-speech for written information recognized in video, and/or the like.

These techniques may be helpful, but are limited in effectiveness. Text to speech does nothing to help vision. Current contrast, brightness and color adjustment rely on the user viewing the world entirely on video (rather than directly, through a passive lens such as in normal eyeglasses) and perform these adjustments on the entire video image at once, regardless of where in the eye the damage needs correction. Picture-in-picture may be a great help to some but not to others, depending on where in the eye and what type of problems the user suffers from. Current visual aid devices are also not able to view the interior of the eye and determine what aid may be needed at any given location within the eye. Instead, current visual aid devices rely on a physician's previous diagnosis, which is obtained by dilating the pupil and viewing the entire eye at once with magnifying lenses, none of which can be performed by the visual aid device. Also, a more accurate form of foveated rendering of images presented to the eye by a display, which takes into account a more precise mapping of the eye, would not only allow for better vision correction but also allow for more efficient provision of data to the display, even for viewers without vision deficiencies.

A conventional technique for addressing some eye conditions is a surgical procedure. However, some of these surgical procedures are not widely applicable, are risky, are frequently unsuccessful, cannot be performed on some people, may only be able to be performed a single time, and the like. Also, eye diseases can continue to degenerate, requiring additional surgeries or, at some point in the disease's progression, the person may not have any good surgical options.

In summary, what is needed is a way to continually diagnose eye conditions and map the interior of the eye in an automated fashion by the visual aid device, and to deliver that information to the physician and/or to act upon that data in an automated fashion with precise and individualized actions in response to the different conditions of particular locations in the eye.

One aspect of the described system and method provides a method, the method including: obtaining, utilizing at least one image capture device, at least one image of an eye of a user, where that image is obtained by synchronizing light from a display aimed particularly at a given area of the eye with photography of that particular area, the above being performed in a repetitive manner across the entire extent of the eye's interior; identifying, from the at least one image, a plurality of characteristics of the eye; generating, based upon the plurality of characteristics of the eye, a plurality of images, wherein each of the plurality of images is generated for a portion of the eye; and presenting, utilizing at least one display device, a plurality of images to the eye, wherein each of the plurality of images is presented to a portion of the eye corresponding to the conditions identified according to an expert system for the image generated of that given portion of the eye.

Another aspect provides an information handling device, the information handling device including: at least one image capture device; at least one display device; a processor operatively coupled to the at least one image capture device and the at least one display device; a memory device that stores instructions that when executed by the processor causes the information handling device to: obtain, utilizing the at least one image capture device, at least one image of a portion of an eye of a user; identify, from the at least one image, a plurality of characteristics of the eye which may include diagnostics based on an expert system which identifies images as evidence of damage or disease, and which includes logic such that it can, over time, improve its diagnostic capacity based on observed image change over time or in response to adjustments in images displayed to the eye or to other observed image change over time or in response to adjustments in images displayed to the eye or to other observed user activity, wherein the portion of the eye captured in an image may include any area of the eye including portions of the pupil, retina, macula, fovea, and conjoined or nearby nerves, tissues, blood vessels, bone, etc. (which may be captured either within the visible light spectrum or areas of the infrared spectrum); generate, based upon the plurality of characteristics of the eye, a plurality of images, wherein each of the plurality of images is generated for a portion of the eye; and present, utilizing the at least one display device, the plurality of images to the eye, wherein each of the plurality of images is presented to a portion of the eye corresponding to the image generated for the given portion of the eye.

Another aspect provides a product, the product including: a computer-readable storage device that stores executable code that, when executed by the processor, causes the product to: obtain, utilizing at least one image capture device, at least one image of an eye of a user; identify, from the at least one image, a plurality of characteristics of the eye, wherein at least one of the characteristics includes a position of a pupil of the eye; generate, based upon the plurality of characteristics of the eye, a plurality of images, wherein each of the plurality of images is generated for a portion of the eye; and present, utilizing at least one display device, the plurality of images to the eye, wherein each of the plurality of images is presented to a portion of the eye corresponding to the image generated for the given portion of the eye.

A BRIEF DESCRIPTION OF THE DRAWINGS

Figure 6:
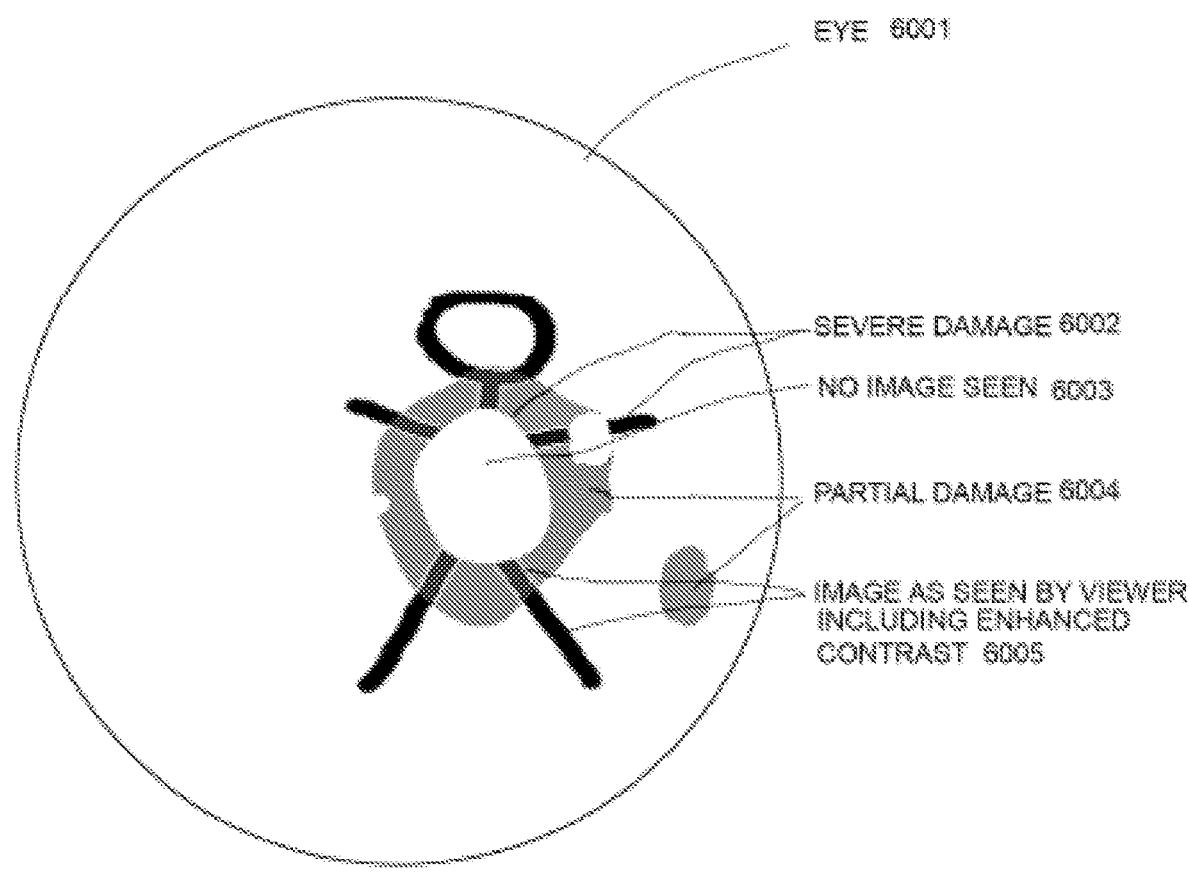
FIG. 6 illustrates the same image as seen in FIG. 5 and the same pattern of macular degeneration, but with enhanced contrast allowing those portions of the image seen in zones of partial macular degeneration to be seen better.

Along with the also-shown contrast enhancement previously illustrated in FIG. 6, the viewer thus sees a comprehensible image.

DETAILED DESCRIPTION OF THE INVENTION

The described system and method provide a technique to generate and present a plurality of images of the interior of the eye, to use those images to diagnose various health conditions, to report diagnoses to a physician or researcher, to improve monitoring and diagnoses in iterative, self-teaching processes, to use the resulting diagnoses to arrange the images on a display device, where the images are based upon characteristics of the eye, and can be blended with natural imagery seen by the eye to enhance or correct the user's visual experience. The system obtains at least one image of an eye of a user using at least one image capture device. The image capture device may use a plenoptic lens array, for example, like those described in commonly owned U.S. patent application Ser. No. 16/436,343, filed Jun. 10, 2019, and titled "NEAR-EYE FOVEAL DISPLAY", which is a continuation-in-part of U.S. patent application Ser. No. 15/671,694, filed Aug. 8, 2017, and titled "NEAR-EYE FOVEAL DISPLAY", which is a continuation-in-part of U.S. patent application Ser. No. 15/594,029, filed May 12, 2017, and titled "NEAR-EYE FOVEAL DISPLAY", the contents of which are incorporated by reference herein. The coordinated image display device may also make use of the above patents and applications and also the software techniques disclosed in commonly-owned U.S. patent application Ser. No. 17/554,779, which is also incorporated by reference herein. The image(s) of the eye may include or identify the position and geometry of the internal areas of the eye, including the full surface of the retina, fovea, cornea, macula, and/or the like, and also may, by using nonvisual wavelengths of light, see more or less deeply into surrounding tissues, bones, blood vessels, nerves, and/or the like.

From the captured image(s) the system can identify a plurality of characteristics of the eye. The characteristics may include a position of a pupil of the eye, characteristics that are indicative of an eye disease and a location of the eye disease within the eye, characteristics that are indicative of an eye condition, and/or the like. With the characteristics, the assistive viewing system can also identify the location of different phenomena across the eye. For example, macular degeneration or retinitis may only affect parts of the eye. As another example, glaucoma may be characterized by a reduced viewing field. Thus, not all the eye may be affected.

The captured images of multiple portions of the eye are made possible by synchronized lighting, from the display, of only those same multiple portions of the eye, while leaving all other areas of the eye unlit. In current examination and captured photographs of the eye, it is necessary to illuminate most or all of the visual field, and often under conditions of extreme dilation of the pupil which lasts for a substantial period of time even after examination is finished or photos have been taken. This is inconvenient for the patient and also does not allow for continual monitoring of the eye while the patient goes about normal activities. The current invention, making use of the above-noted plenoptic lens array, is able to time illumination of an area of the eye as small as a single pixel imaged in a tiny area of the retina with photography of that same area. Furthermore, when the photography is captured by a sensor which has been fitted with the same type of plenoptic array, the exact location and shape of the photographed object can be more accurately mapped because it is seen on multiple locations on the sensor through the multiple lens tiles, allowing for multiple points of triangulation. Also, the system may make this object mapping even more accurate by showing precise image patterns which are then seen by the sensor from multiple angles.

Based upon the characteristics of the eye, the assistive viewing system can generate a plurality of images. Each of the images can be generated for a portion of the eye. This means that the images can be unique for different portions of the eye and dependent upon the characteristics of the portion of the eye to which the image will be presented. As an example, for a portion of the eye that is affected by macular degeneration, the assistive viewing system can generate an image that includes corrections accounting for the macular degeneration. On the other hand, for a portion of the eye that is not affected by macular degeneration, the assistive viewing system can generate an image with no corrections, or corrections that only address other eye conditions, in the event that a person suffers from multiple eye conditions.

These images can then be presented to the eye on a display device. The images are presented in such a manner that it appears to be a cohesive image, even though it is made of multiple images. In other words, the images are presented in a manner that makes it appear to be a single view to the user. Thus, the assistive viewing system can be utilized in a natural environment, much like eyeglasses. As the user is interacting with the world, the user can wear the visual aid device of the assistive viewing system and see the world in a manner more closely to what the person would see if they did not suffer from an eye condition. In other words, like eyeglasses or contacts can be utilized to account for a person having near-sightedness or far-sightedness, thereby allowing the person to see the world as if they do not suffer from these eye conditions, the described system and method can be utilized to account for eye diseases or other eye conditions.

The system also allows benefits even for users who don't suffer from any health conditions, as well as for some who suffer from health issues not typically seen as affecting vision. It allows a superior method of bringing the coordinated multiple images from the plenoptic display system into precise focus and multiple image tile alignment into a single overall image. This is because it offers a new capability not only to accurately track the position of the pupil (as detailed in a previous cited application and/or patent), it also enables the measurement and tracking of the pupil's position relative to the exact distance from the pupil to each of many particular areas of the retina. Every person's eye is slightly different in size, so that the relative angles from each image tile in the display, through the plenoptic lens, will reach a slightly different area of the retina for each person. The described system and method corrects for that, and also corrects the imagery for focus based on each person's differing measurements from pupil to retina. Furthermore, when the eyeglasses in which the plenoptic system is installed are positioned at different distances and angles to the eye, the described system and method can more accurately adjust the alignment of the multiple tiles images so that they blend together properly and correct most accurately for any distortions associated with lens geometries.

The same synchronized display and image capture system allows for accurate monitoring of blood pressure and other health conditions by being able to detect rapid changes in the shape of blood vessels and nerves. It may also provide visual stimuli and measure reactions to those in rapid and continuously timed sequences (for example, at normal video frame rates such as 60 Hz). Common commercially available OLED, LCD, and microLED displays are capable of illuminating the eye at wavelengths that extend significantly into the near infrared (NIR) range, which can allow objects to be seen by commonly available infrared sensors fairly deep into tissue that is nontransparent to visible light. The system could equally deploy short wave infrared (SWIR) sensors, such as those used for optical coherence tomography (OCT), to see even deeper into tissue. In this manner, the benefits of accurate, continuous monitoring of a user's eye while the user goes about normal activities can be brought to OCT for multiple health conditions.

Figure 1:
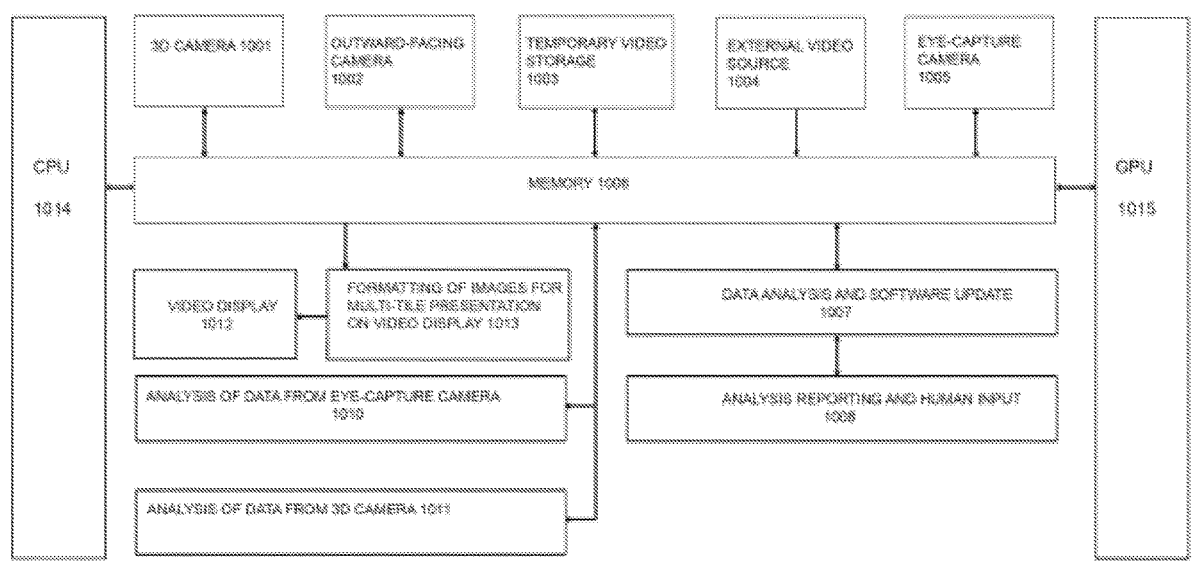
FIG. 1 illustrates a block diagram showing an example apparatus device.

Referring to FIG. 1, a device 1000, for example, that which is used for the visual aid device or used in conjunction with the assistive viewing system, is described. The device 1000 may include any or all of the following: one or more three-dimensional (3D) cameras 1001 aimed either or both inward at the eye and/or outward to capture the objects viewed by the eye (collectively referred to as 3D camera 1001); outward-facing camera 1002 which captures the scene to be viewed; temporary video storage for each video input 1003; external video source(s) 1004; one or more eye-capture cameras or looking into the eye 1005; memory 1006; microprocessors 1014 (collectively referred to as CPU 1014) and graphics processing units 1015 (collectively referred to as GPU 1015) that retrieve data and/or instructions from memory 1006 and execute retrieved instructions in a conventional manner. Memory 1006 can include any tangible computer readable media, e.g., persistent memory such as magnetic and/or optical disks, ROM, and PROM and volatile memory such as RAM.

CPU 1014 and GPU 1015 and memory 1006 are connected to one another through a conventional interconnect 1006, which may be a bus in this illustrative embodiment and which connects CPU 1014, GPU 1015, and memory 1006 to one or more input devices as mentioned above and/or output devices (collectively referred to as video display 1012). Video display 1012 can include one or more displays—such as an OLED (organic light-emitting diode), a microLED, or liquid crystal display (LCD), and/or the like. Both the image capture device(s) and the output devices may include plenoptic lens arrays. As information is fed from memory 1006 to the video display 1012, it is passed through another logical block for formatting of images for multi-tile presentation on the video display 1013. This formatting is partly informed by analysis of data from the eye capture camera 1010, and also by analysis of data from 3D camera 1011. Information from the camera 1011 is analyzed, which leads to updated software, shown as data analysis and software update 1007. Analysis, reporting, and human input 1008 may inform the computer-generated data analysis 1007.

Information handling device circuitry, as for example outlined in FIG. 1, may be used in devices such as tablets, smart phones, personal computer devices generally, and/or electronic devices, which may be used in a system that identifies characteristics of one or more eyes of a user, generates images for the eye of the user based on the characteristics, and presents the images to the eye of the user. Thus, the circuitry may be utilized in image capture devices, display devices, processing components, and/or other components of the assistive viewing device. Additionally, it should be noted that the components illustrated in FIG. 1, may not necessarily be co-located within the same component. Rather, different components may be located in different systems or components of the system. The components may then communicate with each other using wired or wireless communication techniques, including, but not limited to, network communication, short-range wireless communication techniques, near-field communication techniques, and/or the like. Communication may also occur across different data storage and/or data processing locations, for example, local networks, remote networks, cloud networks, and/or the like.

Figure 2:
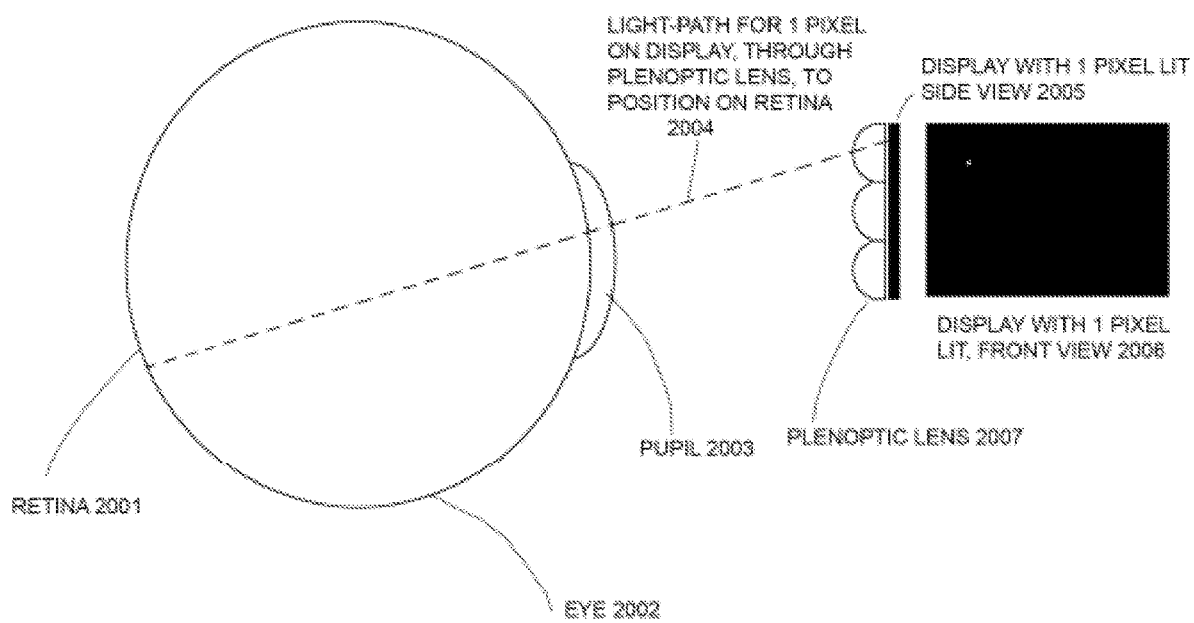
FIG. 2 illustrates an example of a single pixel imaged on the retina.

FIG. 2 illustrates an example of a single pixel imaged on the eye 2002 and particularly on the retina 2001. The retina 2001 sees the pixel at a given location determined by the relative positioning of the pixel as shown on the display (display with one pixel lit, front view 2006 and display with one pixel lit, side view 2005) and focused by the plenoptic lens 2007. The features of the plenoptic lens are such that the beam of light formed by the pixel and lens passes unaffected through the pupil and images directly on the retina, shown as the light-path for one pixel on display, through plenoptic lens, to position on retina 2004. Normal light which is not focused at infinity by the plenoptic lens is instead focused on by the pupil 2003. Either way, the light will image on the retina, but the plenoptic lens and pupil-tracking system incorporated herein allows the light to be aimed particularly at a given spot on the retina no matter the location of the pupil.

Figure 3:
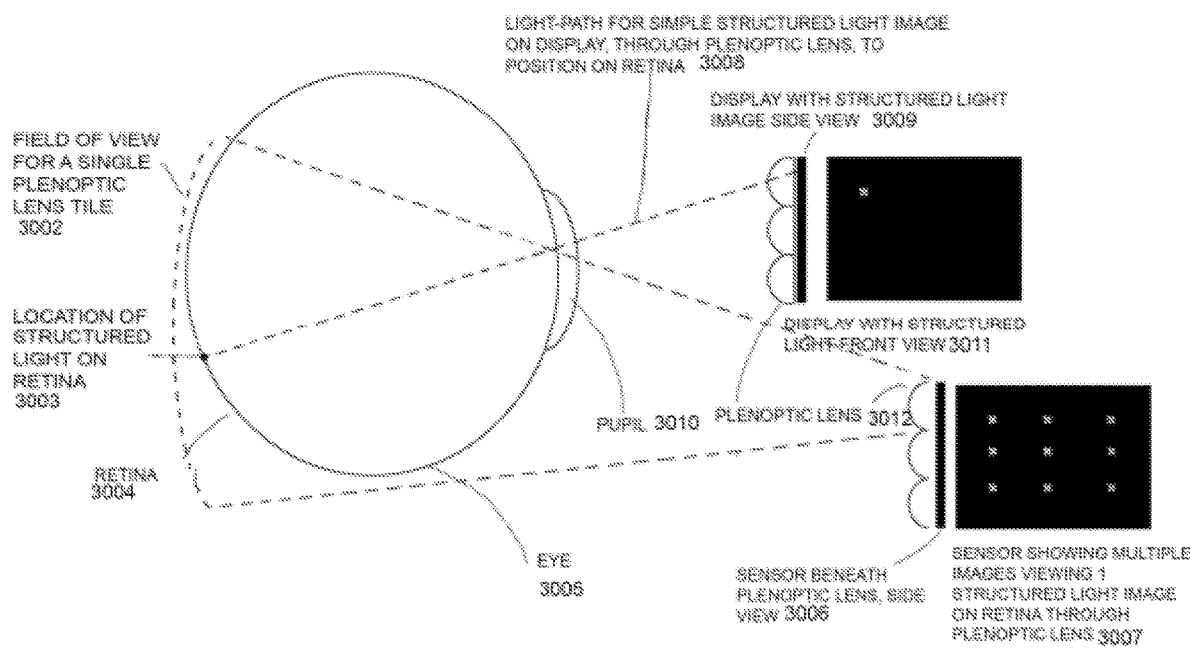
FIG. 3 illustrates an example of a structured-light image, which is imaged accurately on the retina and captured by multiple lens tiles such that multiple triangulations allow three-dimensional location capture.

FIG. 3 illustrates an example of a structured-light image (display with structured light front view 3011, and display with structured light image side view 3009), which enters the eye 3005 through the pupil 3010 and is imaged accurately on the retina (retina 3004 and location of structured light on retina 3003) and then captured by multiple lens tiles through the plenoptic lens 3012 such that multiple triangulation allows location capture (sensor showing multiple images viewing one structured light image on retina through plenoptic lens 3007). As in FIG. 2, it shows an image projected from a display through the plenoptic lens and onto the retina. In this case, however, rather than a single pixel the display shows a pattern. The pattern is viewed by a camera which also features a plenoptic lens, and the resulting image of the pattern is captured multiple times, once through each of multiple plenoptic lens tiles but at different angles, as shown by the angular location of the structured light pattern within the field of view for a single plenoptic lens tile 3002. As will be readily apparent to one versed in the art of creating locational data from more than one angular view of an image, the differing fields of view of each of the multiple tiles and differing angles at which the image is seen allow for a detailed understanding of the shape of the object illuminated by the pattern.

Figure 4:
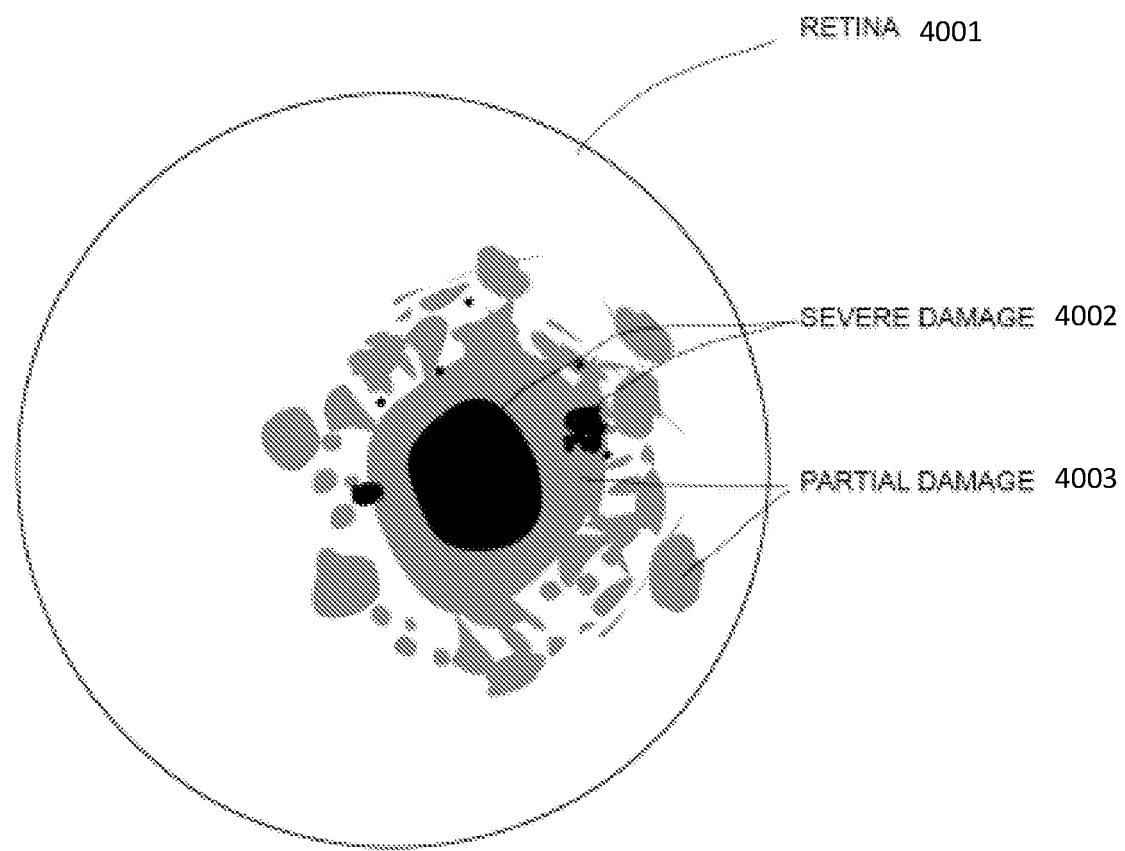
FIG. 4 illustrates a common pattern of macular degeneration, simplified for this illustration, including fully visionless areas as well as areas with some visual ability.

FIG. 4 illustrates a common pattern of macular degeneration on a retina 4001, simplified for this illustration, including fully visionless areas, identified as those areas with severe damage 4002, as well as areas with some visual ability, identified as those with partial damage 4003.

Figure 5:
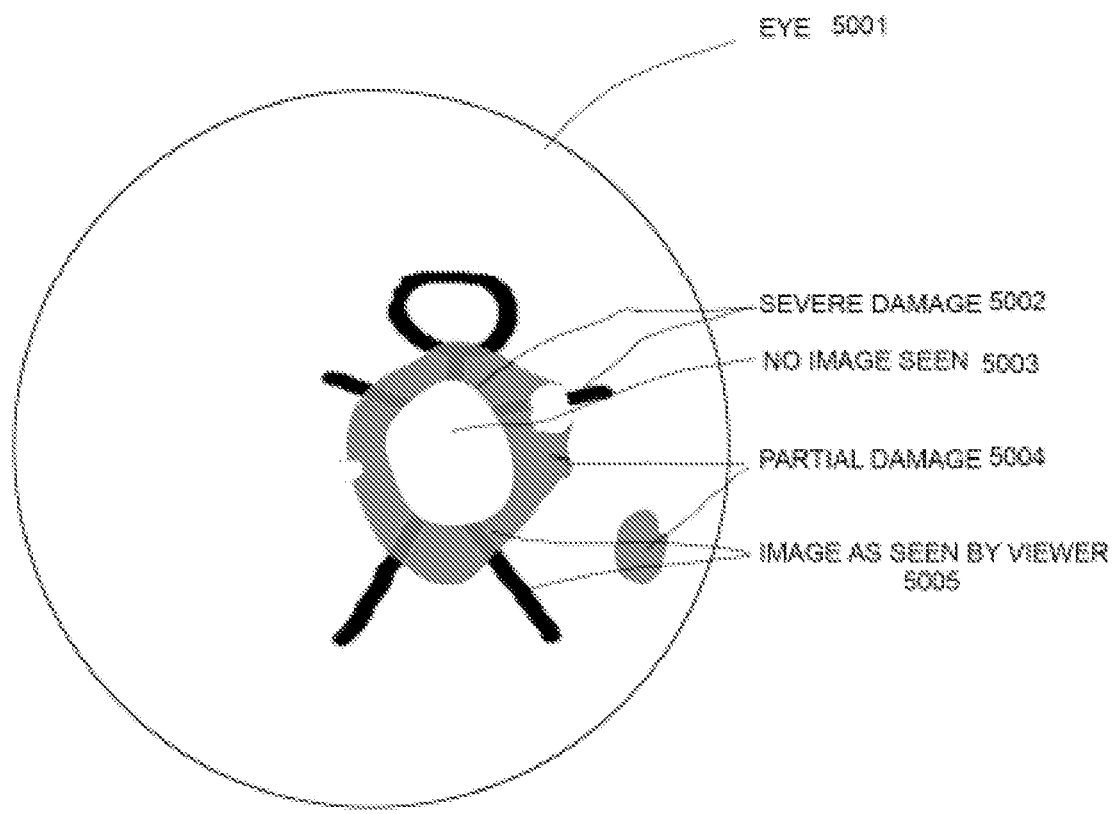
FIG. 5 illustrates an image positioned on the retina in such a way that it is difficult for the person afflicted with a common pattern of macular degeneration to see. The central area of the image falls into the zone of complete degeneration so it goes entirely unseen, while areas of the image falling into the zone of partial degeneration are dimly seen.

FIG. 5 illustrates an image positioned on the eye 5001 in such a way that it is difficult for the person afflicted with a common pattern of macular degeneration to see. As can be seen between FIG. 4 and FIG. 5, the image positioned on the eye 5001 in FIG. 5, is illustrated as if the person is afflicted with the pattern of macular degeneration illustrated in FIG. 4. It is positioned onto areas with severe macular damage 5002 and partial damage 5004. Nothing of the image at all can be seen in the areas of severe damage 5003. The image as seen by the viewer 5005 is soft and hard to differentiate from background imagery (not shown) or no other imagery at all. The central area of the image falls into the zone of complete degeneration so it goes entirely unseen, while areas of the image falling into the zone of partial degeneration are dimly seen. This complete phenomenon is common to the visual experience of many people suffering from macular degeneration.

FIG. 6 illustrates the same image as seen in FIG. 5 and the same pattern of macular degeneration of the eye 6001, but with enhanced contrast allowing those portions of the image seen in zones of partial macular degeneration 6004 to be seen better (image as seen by viewer including enhanced contrast 6005). As seen in FIG. 6, the areas with severe damage 6002 still result in the person not being able to see that portion of the image 6003.

Figure 7:
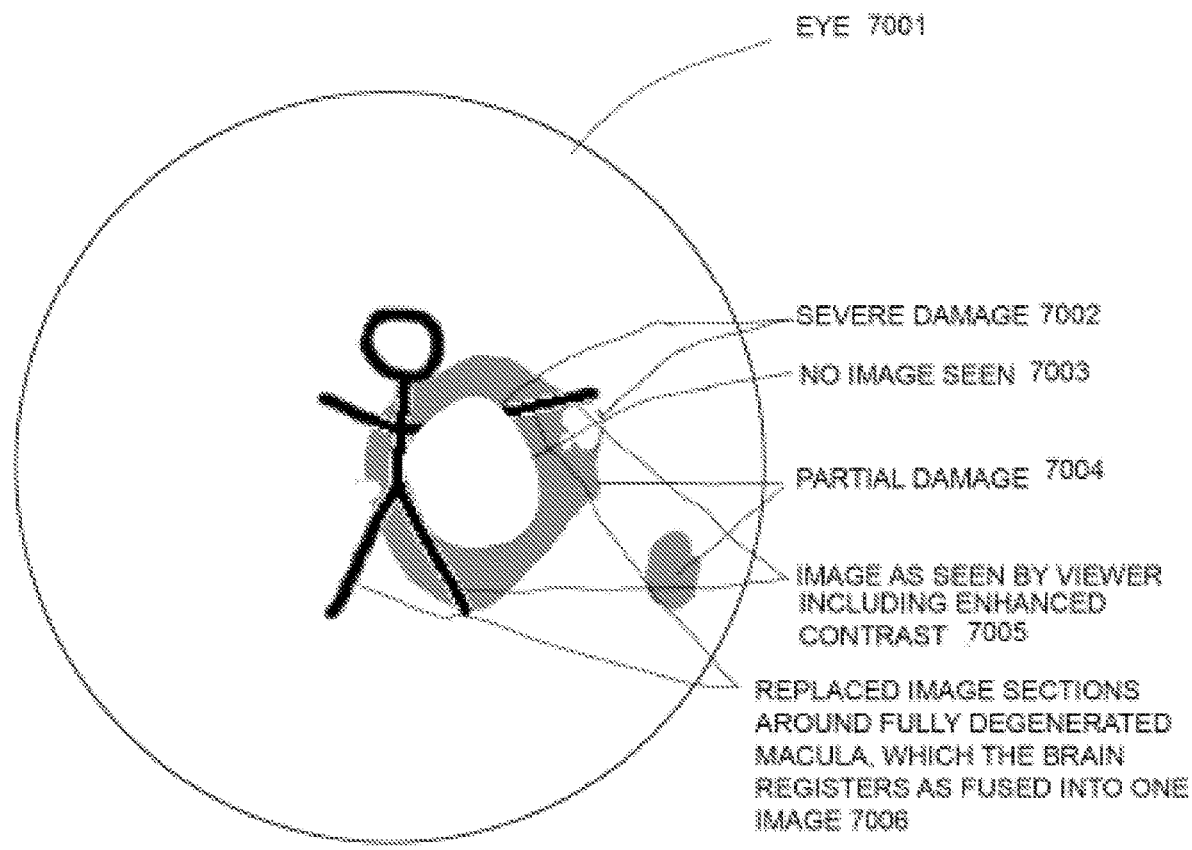
FIG. 7 illustrates the same image as seen in FIGS. 4, 5 and 6, but with portions of the image projected separately onto the retina in a coordinated way such that areas of the retina with no visual ability are avoided, and image portions abut those areas with no visual ability such that the user's brain fuses them into a single contiguous image.

FIG. 7 illustrates the same image as seen in FIGS. 4, 5 and 6, but with portions of the image projected separately onto the retina of the eye 7001 in a coordinated way (replaced image sections around fully degenerated macula 7002, which the brain registers as fused into one image 7006) such that areas of the retina with no visual ability 7002 where no image is seen 7003 are avoided, and image portions abut those areas with no visual ability such that the user's brain fuses them into a single contiguous image. This simplified illustration should also be seen as including some amount of overlap of the multiple images projected separately on the retina. The exact combination of overlap, image sharpening, double or triple or more image exposures and precise organization of the images presented to the eye will vary with the particulars of the vision correction required by the user. Along with the also-shown contrast enhancement previously illustrated in FIG. 6, which allows the viewer to see the image in the partial damage areas 7004 better, the viewer thus sees a comprehensible image. This warped and coordinated discontinuous image, and any associated contrast enhancement, in order to be seen as continuous by the viewer, must continually be adjusted according to gaze tracking performed by the system so that the illusion is maintained. These image displacement techniques have been taught by the cited U.S. patent application Ser. No. 17/554,779.

This is but one example method for presenting a plurality of images to an eye based upon characteristics of the eye. Particularly, the method may be a method that generates images to account for an eye condition of a person utilizing the assistive viewing system, and may not only be used to counter the effects of macular degeneration but also of other conditions that render portions of the eye blind or that render portions of imagery seen by the eye to lack clarity. Such conditions may include retinitis pigmentosa, retinopathy of various kinds, glaucoma, and others. Slightly different techniques may be used for each of these different conditions. For example, to counteract the effects of astigmatism, different sections of the image can be warped in the different ways noted in U.S. patent application Ser. No. 17/554,779, adjusted for angular differences compensating for the differing diffraction encountered in the imperfectly shaped cornea. In all these cases, the exact required image displacement may be obtained either by the cameras focused internally into the eye and also by test patterns which allow the user, or a physician or other human operator, or software deployed in the system, to conform the images shown on the display so that the given eye condition is counteracted. This conformation method may be implemented on a system which includes a processor, memory device, the near-eye display, as well as output devices other than the near-eye display (e.g., other display devices, printer, etc.), input devices (e.g., keyboard, touch screen, mouse, microphones, sensors, biometric scanners, etc.), image capture devices, and/or other components, for example, those discussed in connection with FIG. 1. While the system may include known hardware and software components and/or hardware and software components developed in the future, the system itself is specifically programmed to perform the functions as described herein to generate and present a plurality of images to an eye based upon characteristics of the eye. Additionally, the assistive viewing system includes modules and features that are unique to the described system.

The assistive viewing system may be implemented on a single information handling device or a system of devices. Generally, the user may wear a device, referred to as the visual aid device. These may be in the form of smart eyeglasses, a head-mounted display, an augmented or virtual reality display, and/or the like. The visual aid device may include certain components that are needed near the field of vision of the user, for example, image capture devices, display devices, and/or the like. However, in the interest of processing power, weight of the visual aid device, heat produced by the device, and other considerations, other components may be located in a separate location different from the visual aid device. For example, some processing and or data storage may be conducted or located in a cloud storage or network location, remote network location, local network location, and/or the like. The visual aid device may therefore also include communication components allowing for communication to the other components. These components, including the visual aid device, components located on the visual aid device, and separately located components all work together to make up the assistive viewing system. Thus, the use of the term information handling device, visual aid device, and/or assistive viewing system may refer to a single device or a system of devices.

A machine-learning model, which may be a neural network, decision tree and/or forest, classifiers, random tree forest or classifier, a combination thereof, a combination of machine-learning models, and/or the like, may be utilized in performing one or more acts of the assistive viewing system. For example, one or more machine-learning models can be used to identify eye conditions, identify corrections that need to be made to result in a more natural viewing field for a user, identify images of the eye that need to be obtained, and/or the like. It should be understood that while the terminology may refer to a single machine-learning model, multiple machine-learning models can be utilized in performing one or more functions of the scheduling system. The machine-learning model may include a plurality of layers, including input, output, hidden, a combination thereof, and/or the like, layers. The machine-learning model is very complex and utilizes complicated mathematical computations. Given the highly precise image adjustments taught herein, it should be appreciated that inaccuracies may be expected, but that the system must measure the user's response to these inaccurate corrections, both conscious and unconscious (such as pupil dilation, rapid pupil movement in a direction that may be associated with unconscious attempts to adjust the correction, etc.) and to adjust image compensation accordingly in a self-learning and self-adjustment manner. Due to the complexity of the machine-learning model, it would be impossible to perform the analyses as performed by the model in the human mind.

Additionally, the machine-learning model is trained to or utilized to make predictions on data that has been previously unseen by the model. To make these predictions, the model includes very complicated mathematical computations that would not be performed in the human mind. Rather, the use of a computer and processor, and, possibly a computer and processor that is specific and tuned to the machine-learning model, allows for performing these complex computations, particularly with a speed that allows for performing the complex processing found in and required by the machine-learning model in a time frame that facilitates the use of the machine-learning model for making the predictions. This speed is not possible with a human or even a group of humans. Thus, a human or even a group of humans, even using pen and paper, could not perform the analyses performed by the machine-learning model in a manner that would actually result in making the predictions provided by the machine-learning model on the large amount of data that is received by the assistive viewing system in a length of time that would make the assistive viewing system function as intended.

The machine-learning model may be trained using a training dataset having annotated training data. Annotated training data includes data that the model may make a prediction upon where the data is annotated with the correct prediction. The machine-learning model can learn from the training dataset how data should be classified or the predictions that should be made with respect to particular data. As predictions are made upon non-annotated data, feedback may be provided. Feedback may be provided in the form of a user making a correction, a user providing input regarding the prediction, predictions from other models regarding the same data, and/or the like. The feedback can be automatically ingested by the model to further train the model, thereby making the model more accurate over time. It should be noted that the model can monitor the predictions made by the model to identify the feedback so that a user does not have manually provide the feedback to the model. Thus, while the model may initially be trained with a training dataset, the model can continually be trained as it is deployed using predictions and feedback regarding the predictions. In the case of the eye conditions and identification of field of view corrections based upon the eye conditions, the machine-learning model may be trained using eye condition data and may, therefore, be able to identify associated field of view corrections. Similar training and corresponding predications may be used for other portions of the described system. The machine-learning model also be trained using unsupervised learning techniques, other supervised learning techniques, reinforcement training, a combination thereof, and/or the like.

While the disclosure will refer to an eye of a user, it should be readily understood that the visual aid device will generally cover both eyes of the user, where applicable. Thus, the same method can be used for the other eye of the user. It should be noted that the eyes of the user may suffer from different eye conditions and/or different degrees of an eye condition. Thus, different images may be presented to each eye to account for the eye conditions and degrees of the eye conditions of each eye and even different eye conditions and/or degrees of eye conditions for different portions of an eye.

Additionally, since the assistive viewing system utilizes computer technology, the system can generate and present images very quickly. This allows the system to frequently, continually, or otherwise generate and present images to account for the eye conditions. In other words, as input regarding an eye is received at the system, the system can adjust the images that are presented in near-real time. Thus, the assistive viewing system provides a technique that allows for changes to be made throughout the day, thereby providing a visual aid device that can optimize a viewing experience for the user as eye conditions change. For example, as a user becomes tired, eye conditions may appear to worsen and the system may account for this apparent deterioration in the eye conditions. On the other hand, when the user is refreshed, eye conditions may appear to be better, so the system may account for this apparent restoration of the eye conditions.

As shown in FIG. 3, the assistive viewing system obtains at least one image of an eye of a user utilizing at least one image capture device. The assistive viewing system may utilize one or more image capture devices that are aimed at the eye. The image capture device(s) can focus on the eye so that it can register the position and geometry of all internal areas of the eye, including the full surface of the retina and fovea. It can also make use of infra-red imagery to register the position of various phenomena in the tissue, nerves, blood vessels, and the like, beneath the visible surface of the retina and fovea. Thus, the image(s) allow the assistive viewing system to plot and measure the retina, cornea, internal constituents of the eye, and/or the like. The obtained imagery may also be presented to clinicians and physicians for diagnostics and study, and to guide their input into the system. The image capture device(s) may include a plenoptic lens array and may be, more specifically a plenoptic Stanhope lens array. It should be noted that the system may capture images of different portions of the eye. Portions of the eye may be very small portions. To identify the portion, the system may simply virtually divide the eye into portions that align with the image capture device and/or display device. Additionally, or alternatively, the system may identify portions as corresponding to parts of the eye that all have the same characteristic(s). In this case, portion sizes may vary across the eye. Thus, the image may be an image of the entirety of the eye or may be an image of just a portion of the eye. Thus, even in the case that an image captures the entirety of the eye, a plurality of images may be obtained.

When obtaining the image(s) the system may also emit bursts of light to obtain useful images of the eye. The system may emit a single burst of light, or may emit a plurality of bursts of light that each corresponds to one of a plurality of images that are obtained. The assistive viewing system can not only localize the photography or obtaining of the images of the eye to particular areas of the eye, but can also deliver light to particular areas of the eye, thereby providing for very short bursts of light at tiny areas of the eye for highly localized flash photography so accurate images of the eye can be obtained. The light bursts can be provided in any appropriate wavelength range, including both visible and non-visible spectrum, across whatever gamut is available from the display and software used to drive the display. With a typical red-green-blue (RGB) display and common 10-bit color depth, a wide range of color gamut is available from near-infrared to ultraviolet (though typically ultraviolet emissions are shielded, the same is not true for infrared emissions). Specialized LEDs and other light sources may also be used to emit wavelengths deep into the infrared range, especially short-wave infrared (SWIR), from which useful data may be seen either by the common RGB sensors used in typical camera modules, or by sensors specialized for the infrared range as will be well understood by those versed in the art. The system's capacity to present short bursts of infrared light timed with short sensor exposures, both aimed with precise accuracy at tiny portions of the eye, allows for continual monitoring and positioning in all wavelength ranges for a wide range of conditions. Additionally, patterns of light, commonly known as structured light, may be projected at very brief periods onto the inner surfaces of the eye and time with camera exposures so that the geometry of the eye can be mapped.

The system can continually or frequently capture images of the eye. The frequency at which images are captured can be a default frequency, set by a user, based upon receipt of a trigger event (e.g., movement of the eye; changing of environmental conditions such as light, humidity, barometric pressure, elevation changes, and/or the like; etc.), based upon receipt of an input by the user indicating an image should be obtained (e.g., pressing a button, providing a gesture, providing a word or phrase, etc.), and/or the like. Thus, the assistive viewing system may include components that can measure different environmental conditions (e.g., humidity sensors, pressure sensors, light sensors, etc.), receive user inputs (e.g., buttons, gesture detection, microphones, etc.), biometric sensors, and/or the like.

At 3006, the assistive viewing system can identify a plurality of characteristics of the eye from the image(s) obtained at 3012. The characteristics may include identifying a position of the pupil with respect to the entire eye. The characteristics may include a geometry of the eye, as identified from the obtained images. In addition to identifying an accurate position of the pupil, the system can also identify the position of phenomena across the eye, which may be indicative of a trait associated with at least one disease. Thus, the phenomena may be a characteristic. In some eye conditions or diseases, phenomena are found in the eye. For example, in the example of macular degeneration, fatty deposits, leaky blood vessels, and/or the like, may be present in or across the eye or portions of the eye. The system can not only identify these phenomena, referred to as characteristics, but can identify the specific location of these phenomena across the eye. Macular degeneration, for example, may present in various discontinuous or partly continuous areas of the eye while leaving other areas with relatively good vision. Glaucoma, as another example, may reduce the field of view of the user. Thus, the system can identify which portions of the eye are affected by a particular eye condition.

Similarly, the system can identify characteristics that are indicative of eye conditions other than eye diseases, for example, visual acuity characteristics which may be indicative of near-sightedness, far-sightedness, astigmatism, and/or the like. For example, the distance from fovea to pupil is determinant of near-sightedness or far-sightedness. This distance may be measured precisely by the described system and method. As another example, pupil dilation, pupil location, blood vessel engorgement, and many other characteristics, may change when the user sees an object in focus as opposed to when the user sees certain objects in different areas of the field of view, under different lighting conditions, and/or the like. Thus, the system can identify not only the characteristics of the eye that are indicative of visual acuity, but also that are indicative of many other health conditions.

Since the assistive viewing system is capable of continual real-time monitoring of the full inner geography of the eye, the assistive viewing system can be used to monitor other characteristics of the eye, for example, blood pressure readings and other attributes that may be indicative of health problems, for example, diabetic retinopathy, angiography, and/or the like. Additionally, the localized flash photography and wide range of color gamut allows for identifying fluorescence characteristics of the eye and in particular areas of the eye which may aid in health monitoring. Thus, the characteristics identified at 3006 and 1010 may include any characteristics that may aid in detecting eye conditions, health conditions, and/or the like.

At 1013, the assistive viewing system determines if images can be generated to account for the characteristics. To determine if images can be generated, the assistive viewing system may map details of the eye from the at least one image. This mapping may result in a virtual or digital reconstruction of the eye including all characteristics of the eye, including the phenomena. Based upon this virtual or digital reconstruction, the system can determine if images can be generated that would account for or address the characteristics of the eye. For example, the system may compare the virtual or digital reconstruction of the eye or portions of the reconstructed eye to a database that may include sets of characteristics and images or image attributes that can be applied to assist in compensating for the characteristics. For example, if the system identifies a characteristic as a macular degeneration phenomenon, the database may identify that, to compensate for this, the brightness, contrast, size, and/or the like, of the image should be adjusted. The database may also identify how much the image attribute should be modified to account for the degree of the characteristic.

The assistive viewing system may also, or alternatively, use a rules engine. With a rules engine, the characteristic is fed to the rules engine and the rules engine analyzes the characteristic(s) against rules generated by or contained within the rules engine. The rules engine then outputs a set of image attributes that should be applied to compensate for the characteristic. As another example, the system may utilize the machine-learning model(s), as described further herein, to determine if images can be generated to account for the characteristics. The machine-learning model(s) may be deployed to analyze the characteristics, including the mapping of the eye, to identify if images could be generated that would account for the characteristics.

It should be noted that the analysis performed in determining if an image or set of images can be generated is fairly complicated because not only is the system determining an output for a single characteristic, but the system can also take into account a plurality of characteristics that can be present at the same time and that can affect the same image attribute and different image attributes at the same time. Additionally, since the system generates at least one image for each of a plurality of portions of the eye at the same time, the analysis becomes more complex because the same analysis is performed across multiple portions of the eye for images that will be all presented at the same time to provide a cohesive image, thereby providing for a corrected viewing field for the user.

If the assistive viewing system determines that images cannot be generated to account for the characteristics, the system may make no changes to the viewing field of the user at 1013. This may occur if the system determines that new images cannot be generated that would fully account for the characteristics. This may also occur if the system determines that the characteristics cause image attributes that cannot be fully applied, for example, because the image attributes conflict with each other. No changes may also be made if the system determines that the currently presented images fully compensate for the characteristics. In other words, the assistive viewing system may be an iterative system which continually monitors the characteristics of the eye and makes small changes to the images that are currently presented to account for any changes in the characteristics. In this case, if no characteristic changes are detected or if the images compensate for the characteristics, then the presented images do not need to be updated, no changes will be made, and the system will continue to present the current images to the user.

If, on the other hand, the assistive viewing system determines that images can be generated to account for the characteristics, the assistive viewing system may generate and present the images to the eye at 1012. In this case, generating and presenting the images may also include updating the currently presented images. Generating the images may include generating an image for each portion of the eye. As previously discussed, eye conditions may only affect a portion of the eye. Accordingly, instead of generating a single direct full image to the entire eye, as found in conventional surgical techniques, the assistive viewing system can generate an image for each portion of the eye.

Generating the image may include applying the rules, database attributes, machine-learning model(s) predictions, and/or the like, as discussed in connection with 1013, to the image for a given portion of the eye. In other words, the system identifies the characteristic(s) for a portion of the eye, determines what image attributes should be applied to account for the characteristics with respect to the portion of the eye, and then generates the image having the identified image attributes for the portion of the eye. Thus, generating the images is performed in view of the characteristics, which may include the mapping of the details of the eye. Once the image(s) are created, the system presents the plurality of images to the eye. Each of the plurality of images is presented to the portion of the eye that corresponds to the image that is generated. In other words, the image that was generated for a particular portion of the eye is presented to that portion of the eye. This may be accomplished by presenting the images to the portion of the eye based upon the mapping of the eye.

Since multiple images are created, the assistive viewing system can join the images into a single overall image, thereby generating a single large field of view within good perceived clarity. To generate the single overall image, the system may warp displayed images to allow them to appear in more accurate focus and/or alignment into the overall image as perceived given the mapped geometry of the eye. The assistive viewing system may deliver multiple overlapping but slightly different images that conjoin into a single overall image, utilizing multiple discontinuous areas of the eye, and fuse the overall set of images created on the eye into a single large field of view with good perceived clarity.

To present the images to the eye, the system may utilize one or more display devices that are aimed at the eye and that are able to deliver properly focused images to any specific area of the eye as desired. The display devices may utilize a plenoptic lens array. The display can pass well-focused images through the pupil without engaging the pupil's focusing muscle and then present those images to any number of specific small sections of the eye, for example, small sections of the retina.

Thus, the assistive viewing system can detect an eye condition and then correct for the eye condition. Examples of this detection and correction follow. However, it should be noted that these examples are non-limiting and other eye condition detection and correction are contemplated and possible. Additionally, multiple eye conditions and corrections may occur at a single time, thereby providing correction for multiple eye conditions for the user with a single visual aid device. Additionally, it should be noted that the eye conditions may be detected using different steps or methods as compared to the following examples. It should also be noted that some of the described examples may be further description of those devices and methods previously described.

Although the Stanhope-plenoptic lens array typically delivers images in focus to most users, no matter their visual acuity, the system (or some outside diagnostics) may determine that a given users' required focus correction is unusually outside the bounds of typical in-focus viewing, in such a case, an additional focusing lens element may be added in front of the plenoptic lens array, or either behind or in front of each of the separate lens tiles in the array, or, as suggested in the associated U.S. applications and patents mentioned herein, the plenoptic lens array may be formed by prism structures within a liquid crystal cell, and the focal length of such lenses may be adjusted to conform to the required correction.

The assistive viewing system may also at least partially automate the detection of a fully focused imaged. As previously discussed, as an eye sees objects in focus, attributes of the eye can change. Thus, the system may present an image and then modify the diopter setting until the system detects the eye attributes that indicate the user is seeing the image in focus. As another example, the distance from the gaze tracking sensor to the pupil, and from the pupil through the typical path of light to the retina, can be measured easily with the assistive viewing system. These distances determine the corrective diopter settings required to compensate for visual acuity eye conditions (e.g., near-sightedness, far-sightedness, etc.). The system may follow the following steps to accomplish this automated diopter setting determination.

These same measurements, both from gaze tracking sensor to pupil and from pupil to retina, allow for a more accurate form of gaze tracking than that commonly used, which measures only from gaze tracking sensor to pupil. This is a key benefit of the described system even for users with no health issues.

The display shows a series of patterns in very short bursts, such as the 1/60th of a second typical video frame rate. Each pattern is seen in multiple positions with the gaze tracking sensor, one position per lens tile. Multiple display colors and non-visible frequencies used in these patterns may also aid in measurement, both of the distance from display to pupil to sensor and of the distance from display to retina to sensor and, thirdly, of the distance from retina to pupil. The images from each sensor tile show the same image, for each image shown on the display, but from different vantage points. In the resultant images, any given point of reflected light in the surface of the pupil or retina will be captured by a sensor pixel in a somewhat different relative position to the image as a whole captured in that tile, depending on the angle of view. The multiple angles of view, and, thus, multiple positions within all tiles with a view of the point of reflected light, are measured relative to each other. This essentially results in multiple triangles with a base on the sensor and display planes which may be the same plane, and apex at the reflecting point are logged. Given that the length of the base of each triangle is known, and that the apex angle is known, the distance from the sensor to the reflective point is easily determinable. The same graphical pattern, measured both as it reflects off the pupil and as it reflects off the retina, when measured for both surfaces, helps assure not only that the distances measured are accurate, but that the shapes of objects (e.g., nodules, growths, blood vessels, etc.) can be mapped accurately. Even if the resolution of the sensor is low, the multiple lens tiles create so many viewpoints, and multiple image patterns in sequence allow so many measurements, that the distance map can be extremely precise, with a 3D image created in computer memory that has far higher resolution than the sensor resolution.

To detect an astigmatism eye condition and appropriate correction, the assistive viewing system may perform the following steps. The cornea is measured by having the display show a series of patterns in very short bursts, such as the 1/60th of a second typical video frame rate. Each pattern is seen in multiple positions with the gaze tracking sensor, one position per lens tile. Multiple display frequencies, both visible and invisible, used in these patterns may also aid in measurement of the user's cornea.

The images from each sensor tile show the same object, for each image shown on the display, but from different vantage points. In the resultant images, any given point of reflected light in the surface of the cornea will be captured by a sensor pixel in a somewhat different relative position to the image as a whole captured in that tile, depending on the angle of view. The multiple angles of view, and thus multiple positions within all tiles with a view of the point of reflected light, are measured relative to each other, thereby essentially creating multiple triangles with a base on the sensor plane and apex at the reflecting point. These angles and positions are all logged.

Given that the length of the base of each triangle is known, and that the apex angle is known, the distance from the sensor to the reflective point is easily determinable. A map of the surface of the cornea can thus be created. Even if the resolution of the sensor is low, the multiple lens tiles create so many viewpoints, and multiple image patterns in sequence allow so many measurements, that the surface map can be extremely precise, with a 3D image created in computer memory that has far higher resolution than the sensor resolution. This surface map can then be mapped onto imagery displayed by the headset, as a typical texture map, which will result in an accurate remapping of imagery so that it fits with the user's particular corneal shape. The result will be a user's view of reality that is corrected and "normal" even for people suffering from a severely misshaped cornea.

This texture map can also be used to model the warping of images, as taught in U.S. patent application Ser. No. 17/554,779, in order to adapt the overall image, small portion by small portion, to compensate for the unwanted ways that the user's cornea bends light. This warp map can then also be adjusted in reaction to gaze tracking so that it continues to conform to the proper image compensation no matter where the user is looking. Similarly, the warp map may also be used for the design of other optics that compensate for the astigmatism, which may be designed out of all typical materials known to optometrists as well as liquid crystal lenses as taught in U.S. Pat. No. 10,520,651 incorporated by reference herein. Either can be molded into a plenoptic lens array that is a passive system, i.e. a plenoptic array of lenses which is used without any display or sensor in back of it, in order to view the world with infinity focus. Each of the lens tiles in this passive array would employ prisms specifically designed to conjoin the multiple lens tiles into a single image, and, warp each tile appropriately to compensate for the user's particular corneal shape. This astigmatic-compensation array may be used as a single element in a pair of eyeglasses, or may be combined with an additional overall lens element to correct for other eye conditions.

The assistive viewing system can also be utilized to perform a visual field test using the following steps. The field of view presented by the plenoptic lens array and the display in back of it must be wide enough for an effective visual field test. With a display horizontal and/or vertical dimension of at least 2 cm, it can allow 180 degrees or more, depending on the distance from the eye at which it is worn; a smaller overall lens array and display may also be shifted in position in front of the eye to measure various aspects of the visual field successively. The field of view can be calibrated via the eye measuring techniques detailed above. The angles determined from retina to pupil will also describe the field of view. Points of light can be shown at brief intervals throughout the visual field. The user would interact with the system to allow a processor and memory to record when the user has or has not seen a given point of light. The points of light can also be timed with video or graphical programming shown on the screen to draw the viewer's attention to a given section of the screen. For example, the system may draw the viewer's attention all the way to the right side of the screen. In this example, the flash of light might then be shown some distance far to the left side of the screen, and, in this way the far-left edge of the user's visual field may be determined.

The assistive viewing system may also be utilized to generate phased regional fundus photography and diagnostics coordinated with timed regional lighting using the following steps. Once the basic geometry of a user's eye is logged, software can then control illumination of a given small section of any of the image tiles so that it is known exactly what area of the retina, fovea, or other portion of the eye, is being lighted. The duration of this illumination can be very short, and timed to an exposure of the camera or other image capture device, exactly as a flash is used for flash photography. The above flash can be timed, also, within video content shown on the overall display such that it occurs when the pupil is aiming at another area of the screen, to minimize disruption or annoyance on the part of the viewer. The flash may also be timed with particular content or with added brightness in the overall display that dilates the pupil to greater extent, to enhance measurement. The flash can be in any color or frequency that the display is capable of showing, for example, in the near infrared, SWIR spectrum, and/or the like. This flash may disclose features of the eye which are not easily visible in white light.

The assistive viewing system may also be utilized to enhance low vision by coordinating image display to appropriate areas of the retina using the following steps. Measurement of the inner eye is used to create a map showing where degeneration of the macula or other retinal damage exists, and how much it has progressed in each area of damage. This map is used as a texture map in software to be overlaid on the basic video image warp that arranges images appropriately for the plenoptic lens array. The goal of this enhancement is to use the lens array to aim conformed warped images. Images may be zoomed out so that the full scene may be seen by the smaller section of the eye with good vision. Images may be aimed at discontinuous useful areas of the retina but warped so as to conjoin in the user's vision. Images may be brightened and/or have contrast added or have colors tinted only in certain areas corresponding the areas of macular or other retinal damage, while other parts of the image that are observed by the viewer in relatively unaffected areas of the eye are not so enhanced.

This may be accomplished in an augmented reality application, either in which one or more of the lenses of the plenoptic lens array allows a view of the real world in focus at infinity while other lens tiles overlay one or more displays, or in which the plenoptic lens array is entirely used to overlay one or more displays while the viewer can see the real world through normal corrective eyeglasses or through no eyeglasses at all. The display seen through the plenoptic lens array may be paired not only with the gaze-tracking camera pointed into the eye but also with one or more cameras pointed outward and capturing video of the world seen by the viewer. Only sections of this video would be shown on the displays, to heighten brightness, contrast, or add color tint to the view of the world seen by the viewer in those areas of her or his vision which are affected by macular degeneration. The rest of the viewer's visual field would not be shown any video.

Another important compensation for macular degeneration or other retinal damage, as noted above, is that images may be aimed at discontinuous useful areas of the retina but warped so as to conjoin in the user's vision. In other words, the described system can project each of the plurality of images separately onto the eye to present an illusion of a single contiguous image as viewed by the user, even though some of the plurality of images may actually be projected onto discontinuous areas of the retina. In order to accomplish this in an augmented reality application, the system must show these discontinuous image warps in such a manner that they do not merely overlay, but replace the view of reality that would otherwise be seen through the system's passive optics (whether plenoptics, common prescriptive optics, or non-corrective lenses, or no lenses at all). This may be accomplished with pixel-by-pixel liquid crystal shutter glasses that are synchronized to the gaze tracking and discontinuous image warps. It may also be accomplished by using a liquid crystal focusing lens, as taught in U.S. Pat. No. 10,520,651, which may also feature pixel-by-pixel prism angle adjustment synchronized with gaze tracking and image warping, such that the perceived natural image falls into line with the desired presented discontinuous image.

The assistive viewing system may also be used to coordinate image display to appropriate areas of the eye to enhance the field of view using the following steps. Gaze tracking is used to continually locate the pupil's position. The user or the system software can control zoom, through any commonly understood feedback to the device such as turning a knob, haptics, recognized eye blinking, and/or the like, so that the overall image is zoomed out to fit the user's field of view. At the edges of the user's field of view, image brightness and contrast are increased in an adjustable roll-up matching the roll-off in the viewer's visual capability, thus extending the user's field of view. This roll-up can be user-controlled or set by a physician.

In an augmented reality application, either in which one or more of the lenses of the plenoptic lens array allows a view of the real world in focus at infinity while other lens tiles overlay one or more displays, or in which the plenoptic lens array is entirely used to overlay one or more displays while the viewer can see the real world through normal corrective eyeglasses or through no eyeglasses at all. The display seen through the plenoptic lens array may be paired not only with the gaze-tracking camera pointed into the eye but also with one or more cameras pointed outward and capturing video of the world seen by the viewer. Only sections of this video would be shown on the displays, to heighten brightness and contrast to the view of the world seen by the viewer in those areas at the edge of the user's field of view. The rest of the viewer's visual field would not be shown any video.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random-access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Additionally, the term "non-transitory" includes all media except signal media.

Program code embodied on a storage medium may be transmitted using any appropriate medium, including but not limited to wireless, wireline, optical fiber cable, radio frequency, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, the method comprising:
    obtaining, utilizing at least one image capture device, at least one image of an eye of a user;
    identifying, from the at least one image, a plurality of characteristics of the eye, wherein at least one of the characteristics comprises a position of a pupil of the eye;
    generating, based upon the plurality of characteristics of the eye, a plurality of images, wherein each of the plurality of images is generated for a portion of the eye; and
    presenting, utilizing at least one display device, the plurality of images to the eye, wherein each of the plurality of images is presented to a portion of the eye corresponding to the image generated for the given portion of the eye.

2. The method of claim 1, wherein at least one of the characteristics comprises a geometry of the eye.

3. The method of claim 1, wherein the at least one characteristic comprises a trait associated with at least one eye disease and wherein the generating comprises generating a plurality of images comprising corrections to address the at least one eye disease.

4. The method of claim 1, comprising mapping, from the at least one image, details of the eye and wherein the generating is performed in view of the mapping.

5. The method of claim 4, wherein the presenting comprises mapping each of the plurality of images to portions of the eye based upon the mapping of the eye and projecting each of the plurality of images separately onto the eye to present an illusion of a single contiguous image as viewed by the user.

6. The method of claim 1, wherein the obtaining comprises emitting at least one burst of light during the capture of the at least one image.

7. The method of claim 6, wherein the emitting comprises emitting a plurality of bursts of light, each of the plurality of bursts of light being emitted to correspond to one of a plurality of images.

8. The method of claim 1, wherein at least one of the at least one image capture device and the at least one display device comprises a plenoptic lens array.

9. The method of claim 1, wherein the at least one image capture device and the at least one display device are located on a visual aid device.

10. The method of claim 1, wherein the at least one display device is located in a line of sight of the eye and wherein the presenting comprises adjusting an alignment of the plurality of images based upon a distance of the at least one display device to the eye.

11. The method of claim 1, wherein at least one of the plurality of eye characteristics comprises a position of the pupil of the eye with respect to other areas of the eye.

12. An information handling device, the information handling device comprising:
    at least one image capture device;
    at least one display device;
    a processor operatively coupled to the at least one image capture device and the at least one display device;
    a memory device that stores instructions that when executed by the processor causes the information handling device to:
    obtain, utilizing the at least one image capture device, at least one image of an eye of a user;

identify, from the at least one image, a plurality of characteristics of the eye, wherein at least one of the characteristics comprises a position of a pupil of the eye;

generate, based upon the plurality of characteristics of the eye, a plurality of images, wherein each of the plurality of images is generated for a portion of the eye; and present, utilizing the at least one display device, the plurality of images to the eye, wherein each of the plurality of images is presented to a portion of the eye corresponding to the image generated for the given portion of the eye.

13. The information handling device of claim 12, wherein at least one of the characteristics comprises a geometry of the eye.

14. The information handling device of claim 12, wherein the at least one characteristic comprises a trait associated with at least one eye disease and wherein the generating comprises generating a plurality of images comprising corrections to address the at least one eye disease.

15. The information handling device of claim 12, comprising mapping, from the at least one image, details of the eye and wherein the generating is performed in view of the mapping.

16. The information handling device of claim 15, wherein the presenting comprises mapping each of the plurality of images to portions of the eye based upon the mapping of the eye and projecting each of the plurality of images separately onto the eye to present an illusion of a single contiguous image as viewed by the user.

17. The information handling device of claim 12, wherein the obtaining comprises emitting at least one burst of light during the capture of the at least one image.

18. The information handling device of claim 17, wherein the emitting comprises emitting a plurality of bursts of light, each of the plurality of bursts of light being emitted to correspond to one of a plurality of images.

19. The information handling device of claim 12, wherein the at least one display device is located in a line of sight of the eye and wherein the presenting comprises adjusting an alignment of the plurality of images based upon a distance of the at least one display device to the eye.

20. A product, the product comprising:

a computer-readable storage device that stores executable code that, when executed by the processor, causes the product to:

obtain, utilizing at least one image capture device, at least one image of an eye of a user;

identify, from the at least one image, a plurality of characteristics of the eye, wherein at least one of the characteristics comprises a position of a pupil of the eye;

generate, based upon the plurality of characteristics of the eye, a plurality of images, wherein each of the plurality of images is generated for a portion of the eye; and present, utilizing at least one display device, the plurality of images to the eye, wherein each of the plurality of images is presented to a portion of the eye corresponding to the image generated for the given portion of the eye.

* * * * *